US00PP15101P2

(12) United States Plant Patent
White

(10) Patent No.: US PP15,101 P2
(45) Date of Patent: Aug. 24, 2004

(54) BERGENIA PLANT NAMED 'APPLE BLOSSOM'

(50) Latin Name: *Bergenia omeiensis*
Varietal Denomination: Apple Blossom

(76) Inventor: Anthony Robin White, Blackthorn Nursery, Kilmeston, Alresford Hants (GB), SO24ONL ( * ) Notice: Subject to any disclaimer, the term of this patent is extended or adjusted under 35 U.S.C. 154(b) by 39 days.

(21) Appl. No.: 10/178,932

(22) Filed: Jun. 24, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya

(57) ABSTRACT

A new cultivar of Bergenia plant named 'Apple Blossom' that is characterized by a mounding habit, large glossy green leaves and abundant clusters of pale pink flowers in early spring. In combination these traits set 'Apple Blossom' apart from all other existing varieties of Bergenia known to the inventor.

3 Drawing Sheets

Genus species: *Bergenia omeiensis.*
Varietal denomination: 'Apple Blossom'.

BACKGROUND OF THE INVENTION

The present invention relates to a new and distinct cultivar of Bergenia grown for use as an ornamental landscape and container plant. The new cultivar is known botanically as Bergenia and will be referred to hereinafter by the cultivar name 'Apple Blossom'.

'Apple Blossom' resulted from a formal breeding program that was developed by the inventor to produce new Bergenia plants that are distinct from the existing varieties. 'Apple Blossom' was bred in a cultivated area of Kilmeston Hants, United Kingdom and selected by the inventor in 1994. The new cultivar was produced by the induced hybridization between the female parent plant which is the species *Bergenia omeiensis* (unpatented) and the male parent plant which is the cultivar known as Bergenia 'Britton' (unpatented). Flower size, stem color and calyx color were the determining criteria by which 'Apple Blossom' was selected.

'Apple Blossom' is characterized by a compact mounding habit, large glossy green leaves, ruby red stems, ruby red calyces and pale pink bell-shaped flowers. The closest comparison plant is the male parent Bergenia 'Britton'. 'Apple Blossom' is distinguishable from both parents by its larger flower size when compared with each parent and by its deeper red stems and calyces when compared with each parent.

The first asexual reproduction was conducted by the inventor, in a cultivated area of Kilmeston Hants, United Kingdom in March 1997. The method used for asexual propagation was division. Since that time the characteristics of the new cultivar have been determined stable and are reproduced true to type in successive generations.

SUMMARY OF THE INVENTION

The following traits have been repeatedly observed and represent the characteristics of the new Bergenia cultivar 'Apple Blossom'. These traits in combination distinguish 'Apple Blossom' from all other commercial varieties known to the inventor. 'Apple Blossom' has not been tested under all possible conditions and phenotypic differences may be observed with variations in environmental, climatic and cultural conditions.

1. Bergenia 'Apple Blossom' exhibits a compact, mounding habit.
2. Bergenia 'Apple Blossom' exhibits large glossy green leaves.
3. Bergenia 'Apple Blossom' exhibits clusters of pale pink bell-shaped flowers held on ruby red stems above the foliage.
4. Bergenia 'Apple Blossom' is floriferous and blooms in early spring.
5. Bergenia 'Apple Blossom' is 60–80 cm. in width and 30–50 cm. in height at maturity in the landscape. When grown outdoors in a 2-liter container, 'Apple Blossom' grows to 45 cm in width and 24 cm in height.
6. Bergenia 'Apple Blossom' is propagated by division and tissue culture.
7. Bergenia 'Apple Blossom' is an ornamental suitable for containers and for use in the landscape.
8. Bergenia 'Apple Blossom' is hardy to below 0° Centigrade.

BRIEF DESCRIPTION OF THE DRAWINGS

The accompanying drawings illustrate the distinguishing traits of the new cultivar 'Apple Blossom'.

The drawing on sheet 1 illustrates the abundant clusters of flowers from a side perspective.

The drawing on sheet 2 is a close-up view of the flowers. The drawings were made of 18-month-old plants grown out-of-doors in Arroyo Grande, Calif. in 2-liter containers. The drawings were made using conventional techniques and although colors may appear different from actual colors due to light reflectance they are as accurate as possible by conventional photography.

BOTANICAL DESCRIPTION OF THE PLANT

The following is a detailed description of 18-month-old plants grown in 2-liter containers out-of-doors in Arroyo Grande, Calif. The color determinations are in accordance with The 2001 R.H.S. Colour Chart of The Royal Horticultural Society London, England, except where general color terms of ordinary dictionary significance are used. Growing conditions, diseases and pests are similar to that of other Bergenia. There are no growing problems known to the inventor.

Botanical classification: Bergenia 'Apple Blossom'.

Commercial classification: Ornamental perennial.

Use: For use in containers, and in the landscape as a border plant or as a groundcover.

Cultural requirements: Plant in partial shade or full sun, but avoid intense sun and heat. Performs best in any well draining soil with regular watering.

Parentage: Bergenia 'Apple Blossom' is a hybrid that resulted from the induced hybridization of the following plants:

*Female parent.*—*Bergenia omeiensis.*

*Male parent.*—Bergenia 'Britton'.

Plant description:

*Bloom period.*—Early spring.

*Plant habit.*—Compact, mounding habit.

*Branching habit.*—Open rosette.

*Vigor.*—Moderate.

*Dimensions.*—At maturity in the landscape: 60–80 cm. in width and 30–50 cm. in height. Grown in 2-liter container: 45 cm. in width and 24 cm. in height.

*Hardiness.*—Hardy to below 0° Centigrade.

*Root system.*—Thick and fibrous.

*Propagation.*—Propagation is accomplished by division and by tissue culture.

*Crop time.*—From division 9 months are needed to produce a finished 1-liter container.

Foliage:

*Type.*—Evergreen.

*Arrangement.*—Alternate.

*Shape.*—Obovate to orbicular.

*Division.*—Simple.

*Apex.*—Rounded.

*Base.*—Cuneate.

*Venation pattern.*—Palmate with depressed veins on the adaxial surface and protruding on veins on the abaxial surface.

*Vein color on mature leaf* (*adaxial surface*).—144B.

*Vein color on mature leaf* (*abaxial surface*).—144D.

*Vein color on young leaves* (*adaxial and abaxial surfaces*).—144A.

*Mature leaf dimensions.*—17.50 cm. in length and 11.50 cm. in width.

*Young leaf dimensions.*—5.50 cm. in length and 4.25 cm. in width.

*Mature leaf margins.*—Crenulate and slightly revolute edges.

*Young leaf margins.*—Crenulate and sinuous.

*Texture.*—Thick and leathery.

*Attachment.*—Petiolate.

*Petiole dimensions.*—8 cm. in length and 0.75 cm. in diameter.

*Petiole surface.*—Glabrous.

*Petiole shape.*—Cylindrical but expanded at base to form sheath.

*Petiole color.*—Surface exposed to sunlight is 178A and surface that is not exposed to sunlight is 144B.

*Mature leaf surfaces* (*adaxial and abaxial*).—Glossy surfaces that are stippled (punctuated with emersed glands).

*Young leaf surfaces* (*adaxial and abaxial*).—Glossy surfaces. Only the abaxial surface is stippled (punctuated with emersed glands).

*Pubescence.*—Absent.

*Young leaf color* (*adaxial and abaxial surfaces*).—The edges of the leaves are 179A and the surface area is a combination of N144B on the apical half and 141A on the basal half.

*Mature leaf color* (*abaxial surface*).—145C with edges that are N144B.

*Mature leaf color* (*adaxial surface*).—141A with edges that are N144B.

*Fragrance.*—Absent.

Flowers:

*Inflorescence type.*—Scapose cyme.

*Flower shape.*—Bell-shaped.

*Aspect.*—Facing downward.

*Petals.*—Five in number.

*Flower color.*—The dark areas range from 76B to 76C and the light areas are 76D.

*Calyx color.*—A combination of 64B and 64C.

*Calyx shape.*—Cupulate.

*Sepals.*—Five in number.

*Sepal color.*—A combination of 64B and 64C.

*Fused or unfused.*—Sepals are erect and fused at base.

*Peduncle.*—Leafless scape.

*Peduncle color.*—64A.

Reproductive organs:

*Stamens.*—10 in numberColor: 161B. Length: 9 mm. Width: 0.5 mm.

*Filaments.*—Color: White. Shape: Linear.

*Anthers.*—Color: 161B. Length: 0.5 mm. Shape: Oval.

*Pistil.*—3 in number. Length: 12 mm. Width at base: 5 mm.

*Pollen.*—Color 161B.

*Stigma.*—3 in number. Color: 166A. Length: 1.5 mm. Width: 2 mm.

*Ovary.*—Position: Partly inferior. Shape: ovoid.

*Carpels.*—Number: 2 (fused at base). Length: approx. 10 mm.

*Fruit.*—Many seeded (20–50 seeds) capsule, non fleshy. Color: Brown, approx 200D.

*Seed.*—Small, approx. 0.5 mm long, 0.5 mm wide. Color: N187. Shape: flattened and round. Surface: rugose.

I claim:

1. A new and distinct cultivar of Bergenia plant named 'Apple Blossom' as described and illustrated herein.

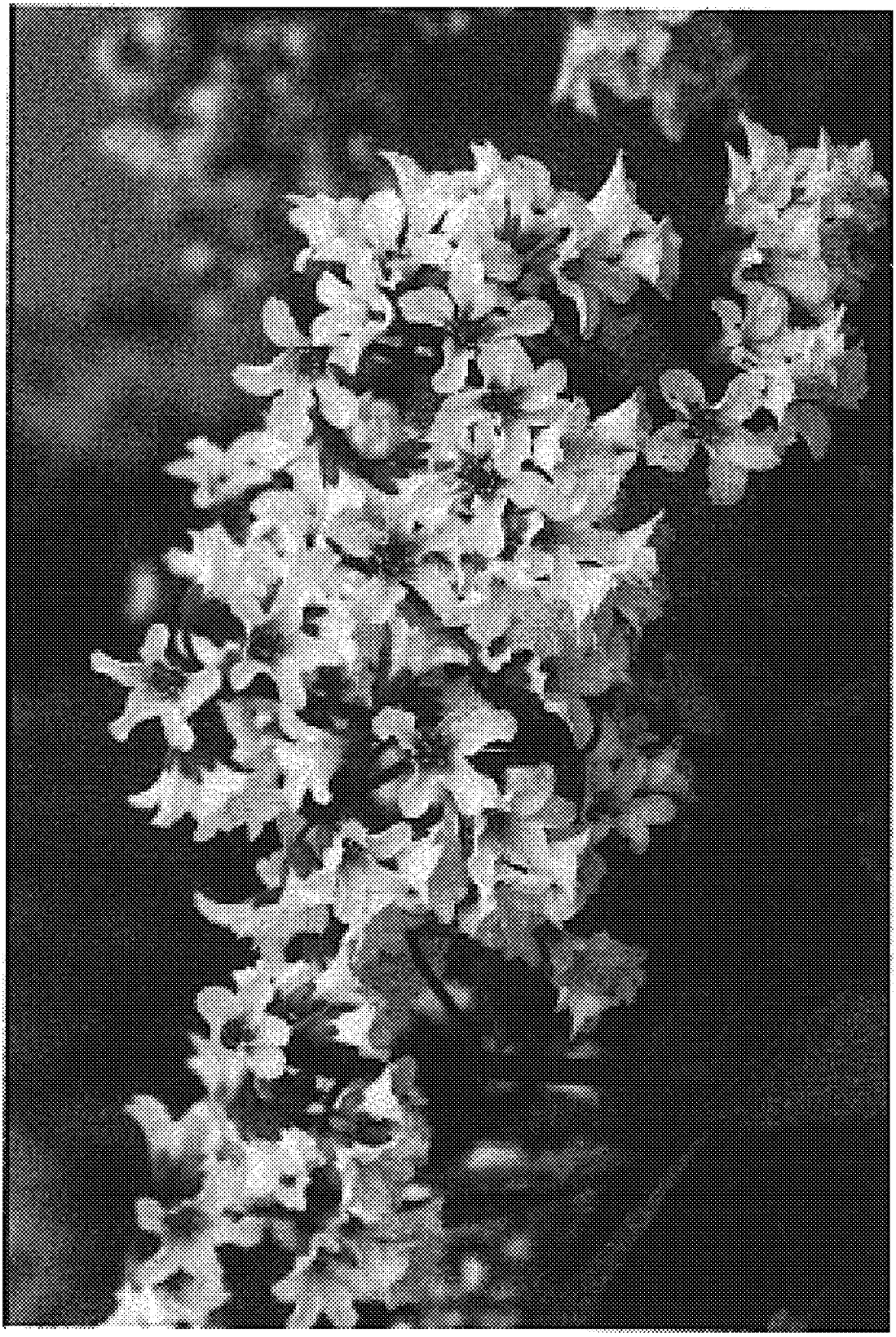

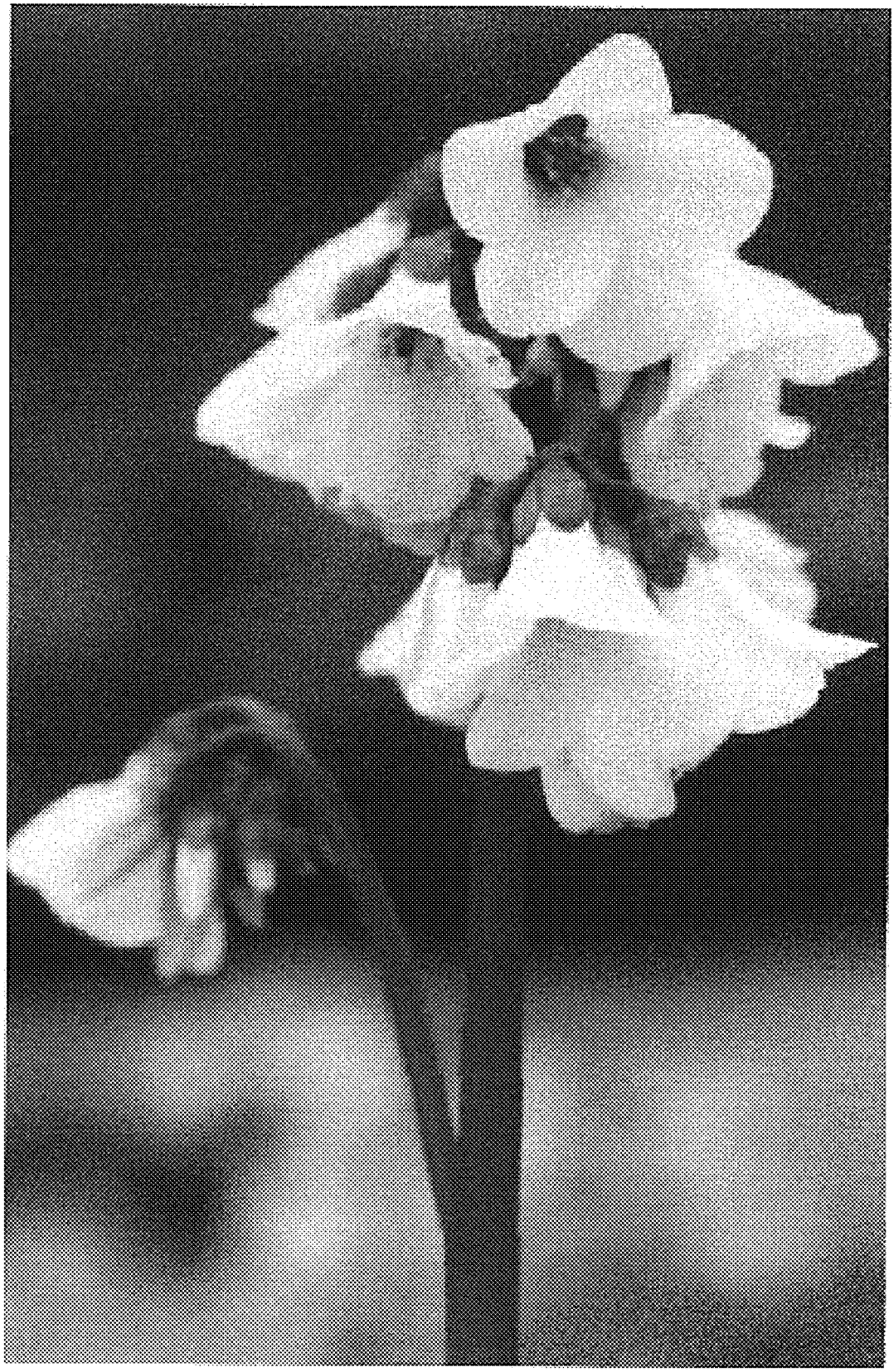

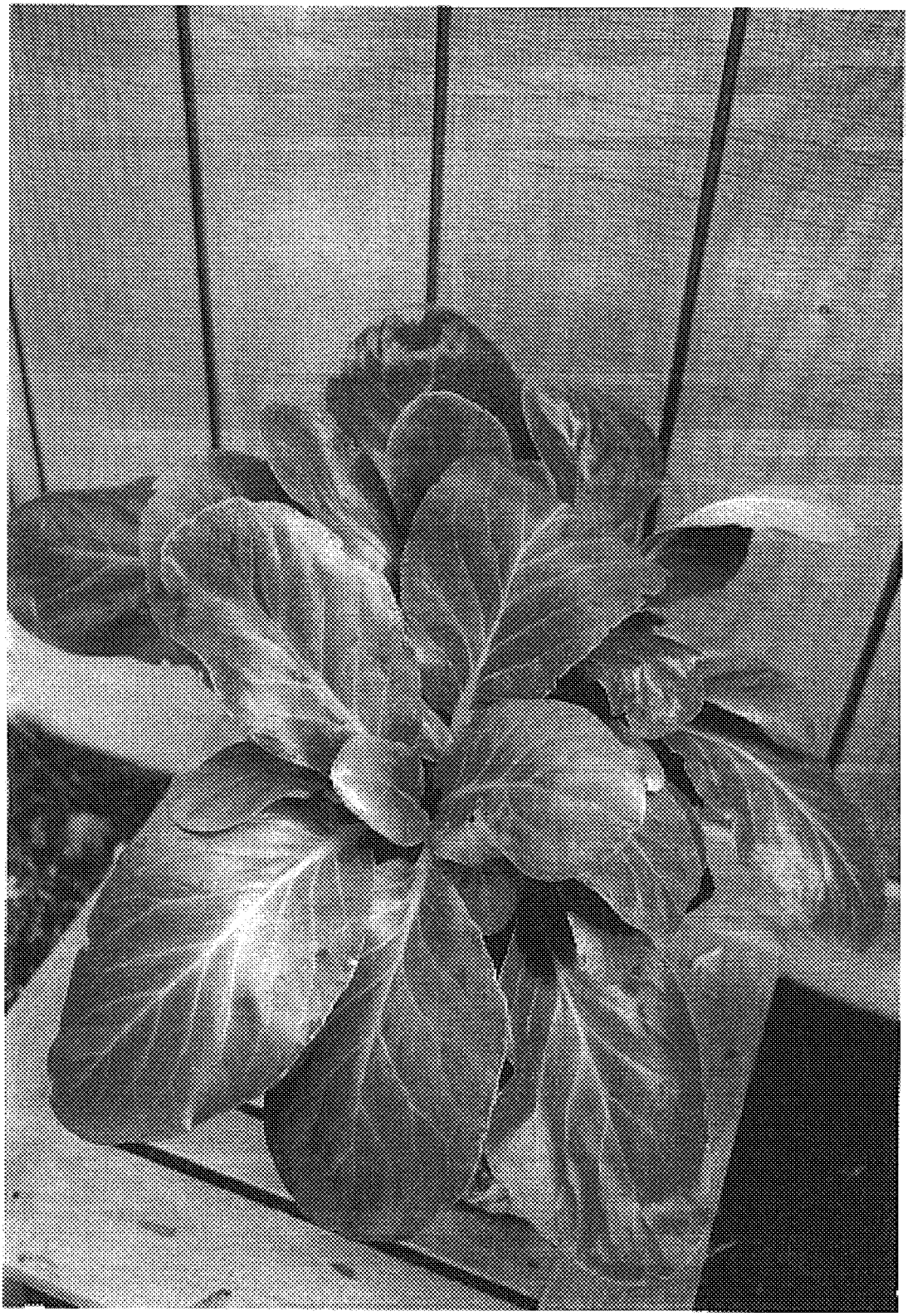

* * * * *